(12) United States Patent
Braddock, Jr. et al.

(10) Patent No.: US 8,409,287 B2
(45) Date of Patent: Apr. 2, 2013

(54) INTERVERTEBRAL PROSTHETIC SYSTEMS, DEVICES, AND ASSOCIATED METHODS

(75) Inventors: Danny H. Braddock, Jr., Germantown, TN (US); Erica M. Gray, Memphis, TN (US); Clinton R. Jacob, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 364 days.

(21) Appl. No.: 12/784,747

(22) Filed: May 21, 2010

(65) Prior Publication Data

US 2011/0288645 A1 Nov. 24, 2011

(51) Int. Cl.
*A61F 2/44* (2006.01)

(52) U.S. Cl. .................... 623/17.15; 623/17.16

(58) Field of Classification Search .... 623/17.11–17.16; 606/248, 249, 324
See application file for complete search history.

(56) References Cited

U.S. PATENT DOCUMENTS

| | | | | |
|---|---|---|---|---|
| 4,759,769 A * | 7/1988 | Hedman et al. | ............ | 623/17.13 |
| 5,236,460 A * | 8/1993 | Barber | ................ | 623/17.15 |
| 6,063,121 A * | 5/2000 | Xavier et al. | ............ | 623/17.15 |
| 6,093,205 A * | 7/2000 | McLeod et al. | ............ | 623/17.16 |
| 6,287,308 B1 | 9/2001 | Betz et al. | | |
| 6,733,531 B1 | 5/2004 | Trieu | | |
| 7,001,431 B2 * | 2/2006 | Bao et al. | ............... | 623/17.12 |
| 7,235,101 B2 * | 6/2007 | Berry et al. | ............... | 623/17.11 |
| 7,588,592 B2 | 9/2009 | Winslow | | |
| 7,682,395 B2 * | 3/2010 | Casey | ............... | 623/17.13 |
| 7,955,392 B2 * | 6/2011 | Dewey et al. | ............ | 623/17.16 |
| 8,114,160 B2 * | 2/2012 | Janowski et al. | .......... | 623/17.14 |
| 2004/0098131 A1 * | 5/2004 | Bryan et al. | ............... | 623/17.15 |
| 2005/0165484 A1 * | 7/2005 | Ferree | ................. | 623/17.11 |
| 2005/0203512 A1 | 9/2005 | Hawkins et al. | | |
| 2006/0241615 A1 | 10/2006 | Melkent | | |
| 2006/0247640 A1 | 11/2006 | Blackwell | | |
| 2006/0247650 A1 * | 11/2006 | Yerby et al. | ................ | 606/90 |
| 2006/0271194 A1 * | 11/2006 | Zucherman et al. | ....... | 623/17.11 |
| 2007/0010813 A1 | 1/2007 | Zucherman et al. | | |
| 2007/0032790 A1 * | 2/2007 | Aschmann et al. | ............ | 606/61 |
| 2007/0191957 A1 * | 8/2007 | Anderson et al. | .......... | 623/17.16 |
| 2007/0233253 A1 | 10/2007 | Bray et al. | | |
| 2007/0270961 A1 * | 11/2007 | Ferguson | ................. | 623/17.11 |
| 2008/0009948 A1 * | 1/2008 | Arnin et al. | ................ | 623/17.16 |
| 2008/0027438 A1 * | 1/2008 | Abdou | ......................... | 606/61 |
| 2008/0051890 A1 | 2/2008 | Waugh et al. | | |
| 2008/0177306 A1 * | 7/2008 | Lamborne et al. | ............ | 606/246 |
| 2008/0177390 A1 * | 7/2008 | Mitchell et al. | ............ | 623/17.16 |
| 2008/0183294 A1 * | 7/2008 | Adl | ............................ | 623/17.16 |
| 2008/0288072 A1 | 11/2008 | Kohm | | |
| 2008/0312741 A1 | 12/2008 | Lee et al. | | |

(Continued)

*Primary Examiner* — Eduardo C Robert
*Assistant Examiner* — Lynnsy Schneider (57) ABSTRACT

Intervertebral prosthetic systems, devices, and associated methods are provided. The present disclosure provides top and bottom endplates that engage the lateral walls of the vertebral bodies for stability and incorporate a compliant core, ball-and-socket core, fusion-cage core, or any other suitable type of motion-preserving or fusion cores. The endplate designs allow insertion through a unilateral approach yet still have engagement on both sides of the vertebral body to provide stability and reduce the risk of subsidence. In some instances, saddle style endplates are inserted and then rotated to engage the lateral walls of the vertebral bodies. In other instances, hinged style endplates are inserted in a first orientation and then at least one end portion is pivoted to a second orientation so that the endplates engage the lateral walls of the vertebral bodies.

20 Claims, 9 Drawing Sheets

U.S. PATENT DOCUMENTS

2009/0054991 A1* 2/2009 Biyani et al. ............... 623/17.16
2009/0132054 A1* 5/2009 Zeegers ..................... 623/17.16
2009/0138087 A1 5/2009 Miglietta et al.
2009/0254185 A1* 10/2009 Dollinger ................... 623/17.16
2009/0264927 A1 10/2009 Ginberg et al.
2010/0241231 A1* 9/2010 Marino et al. ............. 623/17.15

* cited by examiner

INTERVERTEBRAL PROSTHETIC SYSTEMS, DEVICES, AND ASSOCIATED METHODS

TECHNICAL FIELD

Embodiments of the present disclosure relate generally to intervertebral implants and associated methods of implantation and treatment.

BACKGROUND

Within the spine, the intervertebral disc functions to stabilize and distribute forces between vertebral bodies. It comprises a nucleus pulposus which is surrounded and confined by the annulus fibrosis. Intervertebral discs are prone to injury and degeneration. For example, herniated discs typically occur when normal wear or exceptional strain causes a disc to rupture. Degenerative disc disease typically results from the normal aging process, in which the tissue gradually loses its natural water and elasticity, causing the degenerated disc to shrink and possibly rupture. Intervertebral disc injuries and degeneration may be treated by fusion of adjacent vertebral bodies or by replacing the intervertebral disc with an implant, also known as a prosthesis or prosthetic device. Generally, fusion of the adjacent vertebral bodies prevents movement between the adjacent vertebrae. Some implants, on the other hand, preserve at least some of the range of motion provided by the natural intervertebral disc.

Although existing devices and methods associated within intervertebral implants have been generally adequate for their intended purposes, they have not been entirely satisfactory in all respects. The intervertebral prosthetic systems, devices, and associated methods of the present disclosure overcome one or more of the shortcomings of the prior art.

SUMMARY

The present disclosure provides intervertebral prosthetic systems, devices, and associated methods.

In one embodiment, an intervertebral prosthetic device is disclosed. The intervertebral prosthetic device includes an upper component for engaging an upper vertebra, a lower component for engaging a lower vertebra, and a central component for positioning between the upper component and the lower component within an intervertebral space between the upper and lower vertebrae. The upper component has an elongated central portion extending along a first longitudinal axis. The elongated central portion is bounded on a first end by a first arm extending substantially perpendicular to the first longitudinal axis and bounded on an opposing second end by a second arm extending substantially perpendicular to the first longitudinal axis. The first arm is configured to engage a first lateral sidewall of the upper vertebra, the second arm is configured to engage a second lateral sidewall of the upper vertebra, and the elongated central portion is sized to extend across an endplate of the upper vertebra between the first lateral sidewall and the second lateral sidewall of the upper vertebra.

The lower component has an elongated central portion extending along a second longitudinal axis. The elongated central portion is bounded on a first end by a first arm extending substantially perpendicular to the second longitudinal axis and bounded on an opposing second end by a second arm extending substantially perpendicular to the second longitudinal axis. The first arm is configured to engage a first lateral sidewall of the lower vertebra, the second arm is configured to engage a second lateral sidewall of the lower vertebra, and the elongated central portion is sized to extend across an endplate of the lower vertebra between the first lateral sidewall and the second lateral sidewall of the lower vertebra.

The elongated central portion, first arm, and second arm of each of the upper and lower components are integrally formed in some instances. In some embodiments, the central component engages each of the upper and lower components with a dovetail interface. In that regard, the central component may be a motion-preserving device or a fusion device. The first arm of the upper component includes an opening for receiving a fastener, such as a bone screw, for securing the first arm to the first sidewall of the upper vertebra. The second arm of the upper component includes a surface treatment for encouraging engagement of the second arm with the second sidewall of the upper vertebra. In some instances, the surface treatment includes a plurality of bone-engaging projections. In one embodiment, the second arm of the upper component is movable between an insertion position (where the second arm extends substantially parallel to the first longitudinal axis) and an anchoring position (where the second arm extends substantially perpendicular to the first longitudinal axis). In that regard, in some instances the upper component includes an actuator adjacent to the second end of the upper component. The actuator is configured to pivot the second arm between the insertion position and the anchoring position.

In another embodiment, a prosthetic system is disclosed. The prosthetic system includes a first component for engaging a first vertebra, a second component for engaging a second vertebra, and a central component for positioning between the first component and the second component within an intervertebral space between the first and second vertebrae. The first component has an elongated central portion extending along a first longitudinal axis. The elongated central portion is bounded on a first end by a first arm extending substantially perpendicular to the first longitudinal axis and bounded on an opposing second end by a second arm. The second arm is movable between an insertion position where the second arm extends substantially parallel to the first longitudinal axis and an anchoring position where the second arm extends substantially perpendicular to the first longitudinal axis. The first arm is configured to engage a first lateral sidewall of the first vertebra, the second arm is configured to engage a second lateral sidewall of the first vertebra when in the anchoring position, and the elongated central portion is sized to extend across an endplate of the first vertebra between the first lateral sidewall and the second lateral sidewall of the first vertebra.

The second component has an elongated central portion extending along a second longitudinal axis. The elongated central portion is bounded on a first end by a first arm extending substantially perpendicular to the first longitudinal axis and bounded on an opposing second end by a second arm. The first arm is configured to engage a first lateral sidewall of the second vertebra, the second arm is configured to engage a second lateral sidewall of the second vertebra, and the elongated central portion is sized to extend across an endplate of the second vertebra between the first lateral sidewall and the second lateral sidewall of the second vertebra.

In some instances, the second arm of the second component is also movable between an insertion position where the second arm extends substantially parallel to the second longitudinal axis and an anchoring position where the second arm extends substantially perpendicular to the second longitudinal axis. In some embodiments, the first component includes an actuator positioned adjacent to the second end. The actuator is configured to pivot the second arm between the insertion position and the anchoring position. In one embodiment, the actuator includes a sliding block and a screw configured such that rotation of the screw causes movement of the sliding block along the first longitudinal axis. At least the screw of the actuator is positioned within a recess in the elongated central portion in some instances.

According to another aspect of the present disclosure, an intervertebral device is disclosed. The intervertebral device includes a component for engaging a first vertebra. The component has an elongated central portion extending along a first longitudinal axis. The elongated central portion is bounded on a first end by a first arm extending substantially perpendicular to the first longitudinal axis and bounded on an opposing second end by a second arm. The second arm is movable between an insertion position wherein the second arm extends substantially parallel to the first longitudinal axis and an anchoring position wherein the second arm extends substantially perpendicular to the first longitudinal axis. The first arm is configured to engage a first lateral sidewall of the first vertebra, the second arm is configured to engage a second lateral sidewall of the first vertebra when in the anchoring position, and the elongated central portion is sized to extend across an endplate of the first vertebra between the first lateral sidewall and the second lateral sidewall of the first vertebra. In one embodiment, the component includes a sliding block adjacent to the second end. The sliding block movable to pivot the second end between the insertion position and the anchoring position. In that regard, the sliding block secures the second end in the anchoring position in some instances. The component further includes a threaded member in communication with the sliding block, in some embodiments. Rotation of the threaded member causes movement of the sliding block, which pivots the second end between the insertion position and the anchoring position. The sliding block and the threaded member are positioned within one or more recesses in the elongated central portion in some instances.

In other embodiments, methods of implanting the prosthetic devices and systems of the present disclosure are provided. In some instances, the methods provide a direct lateral approach to inserting the prosthetic devices and systems.

Other features and advantages of the present disclosure will become apparent from the detailed description of the illustrative embodiments of the accompanying drawings.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 1:
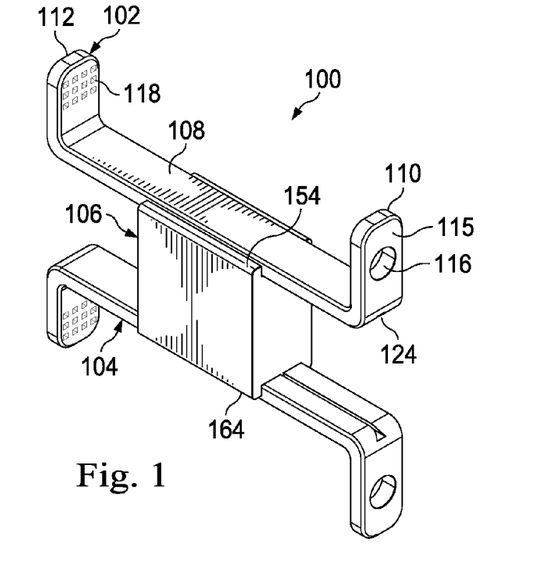
FIG. 1 is a perspective view of an intervertebral prosthetic device according to one embodiment of the present disclosure.
Figure 2:
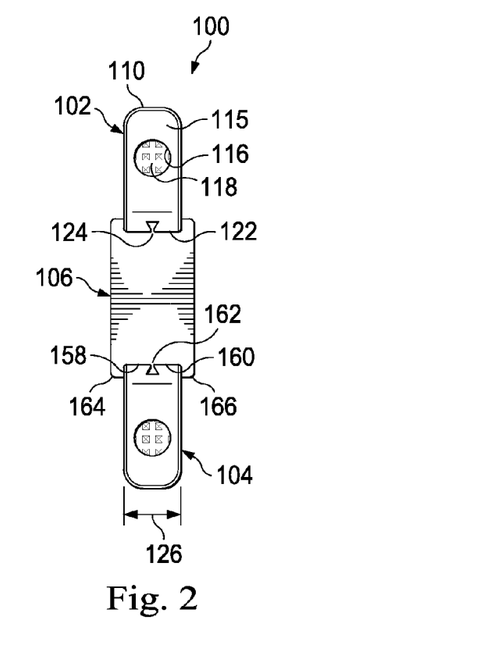
FIG. 2 is an end view of the intervertebral prosthetic device of FIG. 1.
Figure 3:
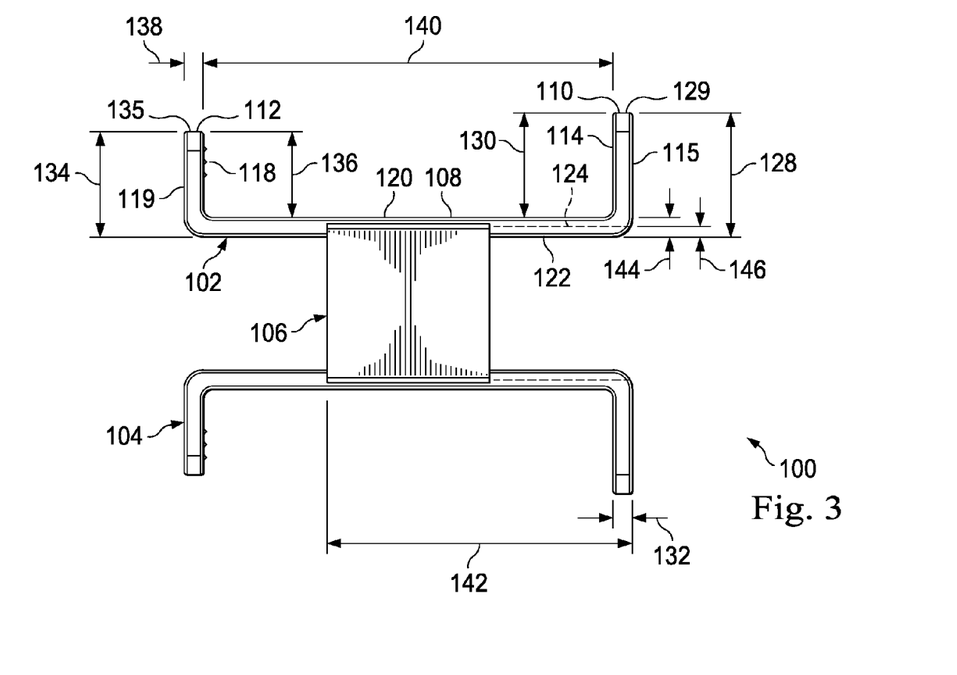
FIG. 3 is a side view of the intervertebral prosthetic device of FIGS. 1 and 2.
Figure 4:
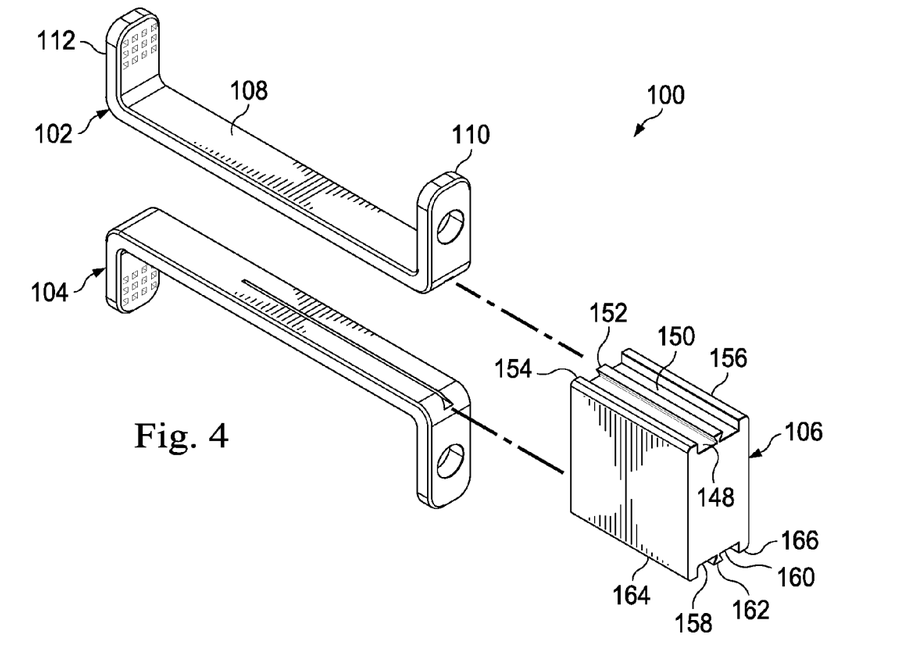
FIG. 4 is an exploded perspective view of the intervertebral prosthetic device of FIGS. 1, 2, and 3.

Referring to FIGS. 1, 2, 3, and 4, shown therein is an intervertebral prosthetic device 100 according to one embodiment of the present disclosure. In particular, FIG. 1 is a perspective view of the intervertebral prosthetic device 100, FIG. 2 is an end view of the device, FIG. 3 is a side view of the device, and FIG. 4 is an exploded perspective view of the device.

The device 100 includes an upper component 102, a lower component 104, and a central component 106. As shown in FIGS. 1, 3, and 4, the upper component 102 includes a central portion 108 bounded by an arm 110 on one end and bounded by an arm 112 on the opposing end. As best seen in FIG. 3, the arm 110 includes a bone-engaging surface 114. The bone-engaging surface 114 is configured to securely engage with a lateral surface of a vertebral body, as described below in greater detail. The arm 110 includes an outer surface 115 opposite the bone-engaging surface 114. As shown in FIGS. 1, 2, and 4, the arm 110 includes an opening 116 extending therethrough from the outer surface 115 to the bone-engaging surface 114. The opening 116 is sized and shaped to receive a bone anchor. The arm 112 similarly includes a bone-engaging surface 118 that is configured to securely engage with a lateral surface of the vertebral body opposite the lateral surface of the vertebral body engaged by the bone-engaging surface 114 of arm 110. The arm 112 also includes an outer surface 119 opposite the bone-engaging surface 118. The central portion 108 also includes a bone-engaging surface 120. In that regard, the bone-engaging surface 120 is configured to engage an endplate of a vertebral body. The central portion 108 includes a surface 122 opposite the bone-engaging surface 120. Within the surface 122 is a recess 124. The recess 124 extends from the outer surface 115 of the arm 110 towards the arm 112.

As shown in FIG. 2, the upper component 102 has a width 126. In some instances, the width 126 is between about 2 mm and about 20 mm and, in some particular instances, is between about 6 mm and about 14 mm. In the illustrated embodiment, the width 126 of the upper component 102 is substantially constant such that the central portion 108, arm 110, and arm 112 each have a width substantially equal to the width 126. However, it is understood that in other embodiments the width 126 of the upper component 102 is varied. In that regard, at least one of the central portion 108, arm 110, and/or arm 112 has a width that is greater and/or less than another of the central portion 108, arm 110, and/or arm 112.

As shown in FIG. 3, the arm 110 has a height 128 between the lower surface 122 and an upper surface 129 of the arm 110. In some instances, the height 128 is between about 2 mm and about 30 mm and, in some particular instances, is between about 4 mm and about 15 mm. The arm 110 has a height 130 between the upper surface 130 and the bone-engaging surface 120. The arm 110 has a width 132 between the bone-engaging surface 114 and the outer surface 115. In some instances, the width 132 is between about 2 mm and about 12 mm and, in some particular instances, is between about 2 mm and about 8 mm. The arm 112 has a height 134 between the lower surface 122 and an upper surface 135 of the arm 112. In some instances, the height 134 is between about 2 mm and about 30 mm and, in some particular instances, is between about 2 mm and about 15 mm. The arm 112 has a height 136 between the upper surface 135 and the bone-engaging surface 120. The arm 112 has a width 138 between the bone-engaging surface 118 and the outer surface 119. In some instances, the width 138 is between about 2 mm and about 12 mm and, in some particular instances, is between about 2 mm and about 8 mm.

In the illustrated embodiment, the central portion 108 has length 140 that extends between the bone-engaging surface 114 of the arm 110 and the bone-engaging surface 118 of the arm 112. In some instances, the length 140 is between about 20 mm and about 80 mm and, in some particular instances, is between about 30 mm and about 70 mm. The recess 124 extends along the length of the intervertebral prosthetic device 100 from the outer surface 115 of the arm 110 towards the arm 112 a distance 142. In some instances, the distance 142 is between about 10 mm and about 80 mm. In that regard, the distance 142 extends between about 20% and about 80% across the length 140 of the central portion 108. The central portion 108 has a thickness 144 between the bone-engaging surface 120 and the surface 122. In some instances, the thickness 144 is between about 2 mm and about 8 mm and, in some particular instances, is between about 2 mm and about 5 mm. In that regard, the recess 124 has a depth 146 from the surface 122. In some instances, the depth 146 is between about 1 mm and about 5 mm and, in some particular instances, is between about 2 mm and about 3 mm. In that regard, the depth 146 is between about 20% and about 60% of the thickness 144.

As seen best in FIGS. 2 and 4, the central component 106 is sized and shaped for engagement with the upper and lower components 102, 104. In particular, the central component 106 includes features for engaging with recesses, such as recess 124, of the upper and lower components 102, 104. In that regard, an upper portion of the central component 106 includes a pair of recesses 148, 150 that define a central projection 152 shaped for sliding engagement with the recess 124 of the upper component 102. In the illustrated embodiment, the recesses 148, 150 are tapered such that the central projection 152 has a dovetail configuration. The recesses 158, 160 also define a pair of outer projections 164, 166 shaped for sliding engagement with outer boundaries of the lower component. Accordingly, engagement of the projection 152 with the recess 124 of the upper component 102 and the engagement of the projections 154,156 with the outer boundaries of the upper component (as best seen in FIG. 2) prevent unwanted disengagement of the central component 106 and the upper component 102.

Similarly, in the illustrated embodiment a lower portion of the central component 106 includes a pair of recesses 158, 160 that define a central projection 162 shaped for sliding engagement with the recess of the lower component 104. In the illustrated embodiment, the central surfaces of the recesses 158, 160 are tapered such that the central projection 162 has a dovetail configuration. The recesses 158, 160 also define a pair of outer projections 164, 166 shaped for sliding engagement with outer boundaries of the lower component. Accordingly, engagement of the projection 162 with the recess of the lower component 104 and the engagement of the projections 164,166 with the outer boundaries of the lower component (as best seen in FIG. 2) prevent unwanted disengagement of the central component 106 and the lower component 104.

It is understood that the engagement features illustrated in the embodiment of FIGS. 1, 2, 3, and 4 is one example of engagement structures for securing the central component 106 to the upper and lower components 102, 104 and that the central component 106 and the upper and/or lower components 102, 104 have other engagement configurations in other embodiments. Generally, any engagement structure that facilitates secure engagement between the central component and the upper and lower components 102, 104 may be utilized. As will be apparent from the discussion below regarding implantation of the intervertebral prosthetic device 100, the engagement structure facilitates introduction of the central component 106 between the upper and lower components 102, 104 after implantation of the upper and lower components. Accordingly, the core or central component is connected to the endplates utilizing mechanisms including, but not limited to a dovetail on the top and/or bottom of the core that engages grooves in the endplates, a groove on the top and/or bottom of the core that engages dovetails in the endplates, tabs on the core that lock into attachment points on the endplates, tabs on the endplates that lock into attachment points on the endplates, brackets attachable to the core and to the endplates, and/or screws for securing the core to the endplates. Further, it is understood that the engagement structure between the central component 106 and the upper component 102 is different from the engagement structure between the central component 106 and the lower component 104 in some instances. Further still, in some embodiments the engagement of the central component 106 with the upper component 102 and/or the lower component 104 facilitates an offset arrangement of the central component relative to one or both of the upper and lower components. An example of one such arrangement is illustrated and described in the context of FIG. 16 below.

The central component 106 of the intervertebral prosthetic device 100 is generally a compliant core, a ball-and-socket core, a fusion-cage core, or other suitable type of motion-preserving or fusion core. In some embodiments, at least the engagement features of the central component 106 are formed of a material having sufficient rigidity to prevent unwanted disengagement from the upper and lower components 102, 104. Accordingly, in some embodiments the engagement features are formed of a material having greater rigidity and/or stiffness than other portions of the core. For example, in some compliant core embodiments the engagement features are formed of a material having greater rigidity and/or stiffness than other portions of the compliant core that provide the desired flexibility and resilience to the compliant core. In some instances, rigid plates are over-molded into the top and bottom portions of the compliant core to facilitate these connections. In that regard, the brackets can be made from a variety of surgical-grade materials, including but not limited to stainless steel, titanium alloy, PEEK, cobalt chrome alloy, and other metal, ceramic, polymer, and/or composite materials. The compliant cores can be made from a variety of surgical-grade materials, including but not limited to polymers such as silicone, polyurethane, and other resiliently flexible materials.

Figure 5:
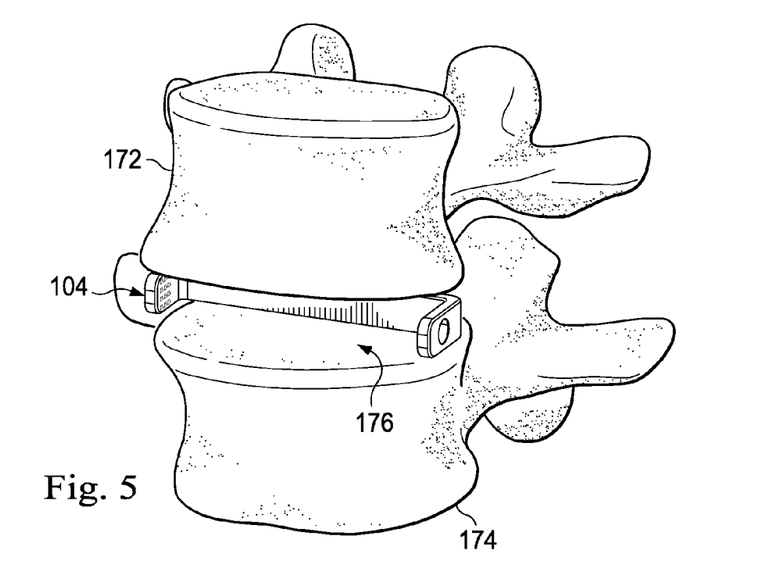
FIG. 5 is a perspective view of an arrangement illustrating implantation of a component of a prosthetic device in an insertion orientation according to one embodiment of the present disclosure.
Figure 6:
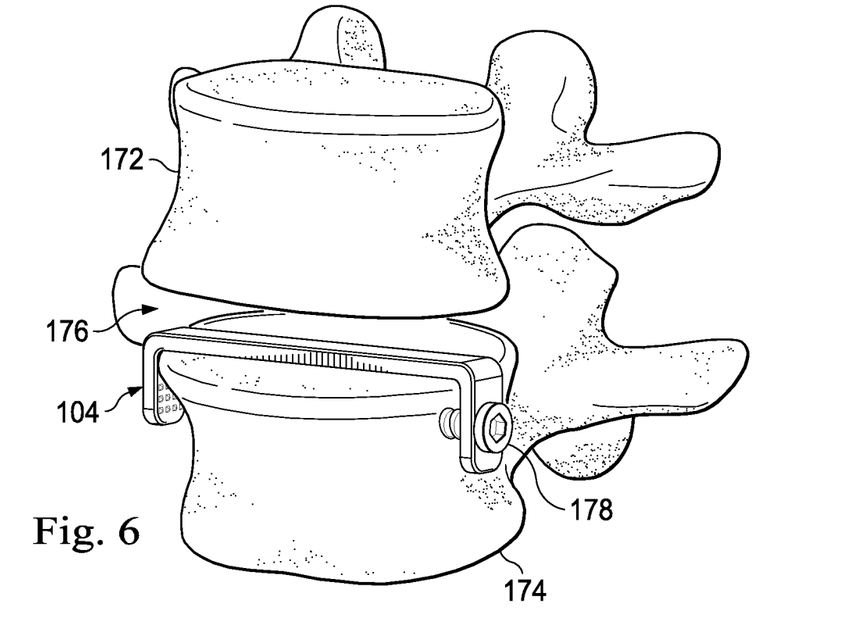
FIG. 6 is a perspective view of the arrangement of FIG. 5 illustrating the component of the prosthetic device fixedly engaged with the lower vertebra in an anchoring orientation.
Figure 7:
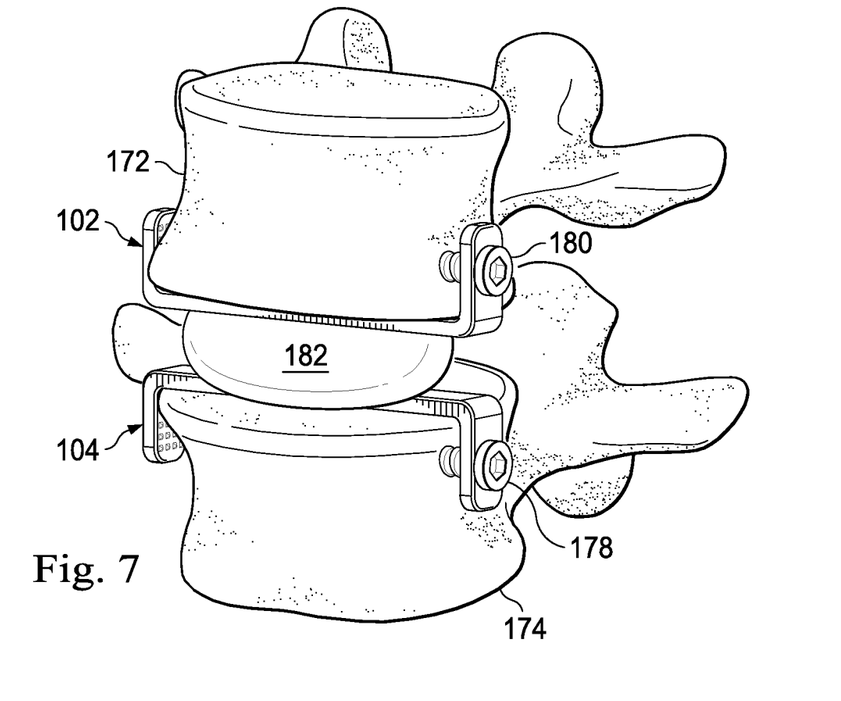
FIG. 7 is a perspective view of the arrangement of FIGS. 5 and 6 illustrating the prosthetic device fully implanted between an upper vertebra and the lower vertebra according to one embodiment of the present disclosure.

Referring now to FIGS. 5, 6, and 7, shown therein are aspects of a method implanting an intervertebral prosthetic device in accordance with the present disclosure. In particular, FIG. 5 is a perspective view of a component of a prosthetic device positioned between an upper vertebra and a lower vertebra in an insertion orientation; FIG. 6 is a perspective view the component fixedly engaged with the lower vertebra in an anchoring orientation; FIG. 7 is a perspective view of the prosthetic device fully implanted between the upper and lower vertebrae and the lower vertebra according to one embodiment of the present disclosure.

Referring more specifically to FIG. 5, the lower component 104 is inserted between an upper vertebra 172 and a lower vertebra 174 in an insertion configuration. The lower component 104 is laterally inserted into the intervertebral disc space 176 between the upper and lower vertebrae 172, 174. In that regard, a discectomy or other procedure for removing all or a portion of the natural disc between the upper and lower vertebrae 172, 174 is performed to create the intervertebral disc space 176 to allow insertion of the lower component 104. As shown, in the insertion configuration of FIG. 5 the arms of the lower component 104 are oriented in a generally anterior/posterior direction such that the lower component has a maximum height that is less than the distance between the endplates of the upper and lower vertebrae 172, 174. In that regard, the insertion configuration allows the leading arm of the lower component 104 to be laterally inserted through the disc space 176 to a position adjacent the lateral sidewall of the lower vertebra 174 opposite from the insertion point. In the illustrated embodiment, for example, the insertion point is on the left lateral side of the patient such that the leading arm of the lower component 104 is passed through the disc space 176 to a position adjacent the right lateral sidewall of the lower vertebra 174. It is understood that in other embodiments the insertion is from the right lateral side of the patient. Further, it is understood that the lateral insertion is either a direct lateral insertion or an oblique lateral insertion.

Referring more specifically to FIG. 6, after the lower component 104 has been inserted into the disc space 176 and the leading arm positioned adjacent the opposite lateral sidewall of the lower vertebra 174, the lower component 104 is rotated to an anchoring configuration such that the arms of the lower component 104 extend downward for engagement with the lower vertebra 174. In the illustrated embodiment, the lower component 104 is rotated approximately 90 degrees along a longitudinal axis of the lower component between the insertion configuration and the anchoring configuration. In the anchoring configuration the leading arm of the lower component 104 engages the opposing sidewall of the lower vertebra 174 and the trailing arm of the lower component is positioned for engagement with the near sidewall of the lower vertebra. In that regard, the lower component 104 is sized such that the central portion of the lower component spans across the endplate of the lower vertebra 174 and the two arms engage the opposing sidewalls of the lower vertebra. In some instances, a plurality of lower components of varying sizes are provided and medical personnel selects the appropriate sized lower component based on the anatomy of the patient.

With the lower component 104 in the anchoring configuration, a bone anchor 178 is inserted through the opening in the trailing arm of the lower component and into engagement with the lower vertebra 174. In the illustrated embodiment the bone anchor 178 is a bone screw. The bone anchor 178 fixedly secures the lower component 104 to the lower vertebra 174. Generally, the bone anchor 178 may be any bone anchor capable of securing the lower component 104 to the lower vertebra 174 including screws, staples, pins, or otherwise.

Figure 17:
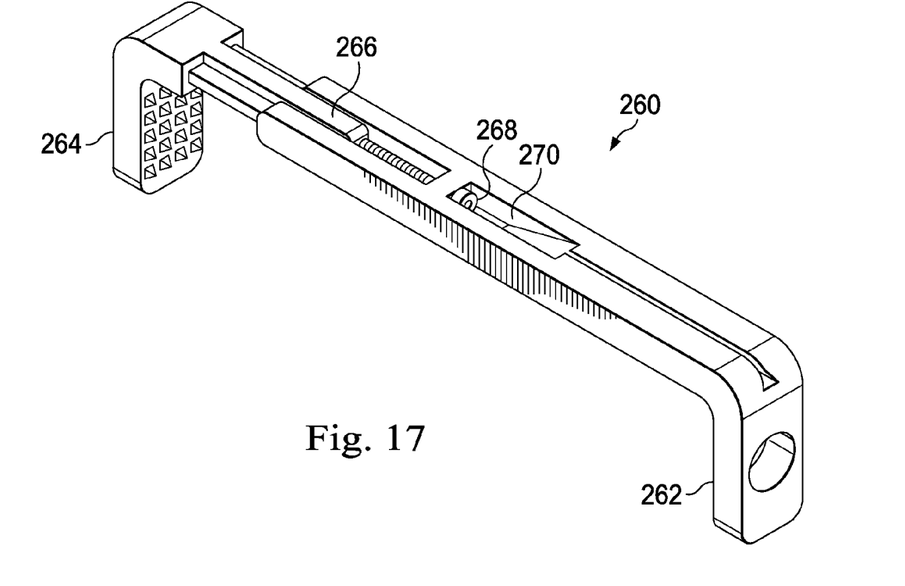
FIG. 17 is a perspective view of an endplate component of a prosthetic device in a lengthened configuration according to another embodiment of the present disclosure.
Figure 18:
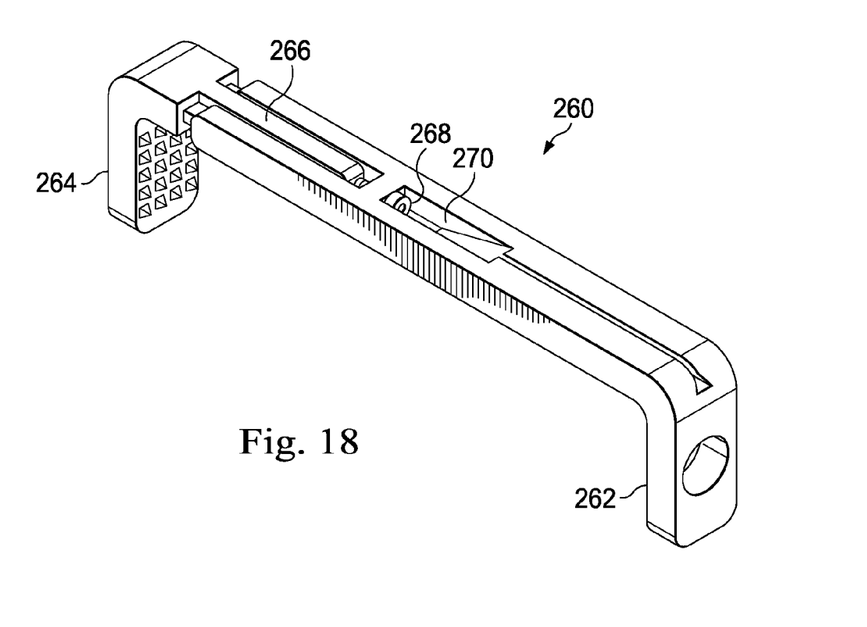
FIG. 18 is a perspective view of the endplate component of the prosthetic device illustrated in FIG. 17 in a shortened configuration.

In other embodiments, the lower component is adjustable such that the distance between the arms is modifiable to fit a variety of vertebra sizes. For example, in one embodiment the lower component is comprised of two pieces slidingly engaged with one another. One of the arms of the lower component is associated with each of the two pieces such that when the pieces are slidingly expanded or retracted relative to one another the distance between the arms correspondingly increases or decreases. In this manner the lower component can be adjusted to properly fit a variety of vertebrae. In some embodiments, the separation of the arms is controlled by a mechanical engagement between the pieces of the lower component. For example, in some instances a sliding block configuration similar to the one described below in the context of the pivot mechanism of FIGS. 10-15 is utilized to adjust the distance between the arms of the lower component. Accordingly, in such an embodiment, with the lower component in the anchoring configuration and the central portion of the lower component is engaged with the endplate of the lower vertebra, the distance between the arms is adjusted such that the arms fixedly engage the sidewalls of the lower vertebra 174. The endplate component discussed below with respect to FIGS. 17 and 18 is one example of such an adjustable component.

In some instances, the bone anchor 178 is inserted through the opening in the trailing arm after engagement of the arms with the sidewalls. In other instances, however, the compression caused by decreasing the distance between the arms to cause engagement with the sidewalls of the lower vertebra 174 is sufficient to maintain the lower component in fixed engagement with the lower vertebra without use of the bone anchor 178. In that regard, one or both of the arms of the lower component include engagement features to facilitate fixed engagement with the lower vertebra 174 in some instances.

Referring more specifically to FIG. 7, the upper component 102 is secured to the upper vertebra 172 in a similar manner as to how the lower component 104 is secured to the lower vertebra 174. Specifically, the upper component 102 is laterally inserted into the disc space 176 in an insertion configuration, rotated to an anchoring configuration, and fixedly secured to the upper vertebra 172. In the illustrated embodiment, a bone anchor 180 is inserted through the opening in the trailing arm of the upper component and into engagement with the upper vertebra 172. It is understood that the upper component 102 may be inserted before, after, or simultaneously with the lower component 104.

Once the upper and lower components 102, 104 are secured to the upper and lower vertebra 172, 174, respectively, a central component 182 is inserted into the disc space 176 between the upper and lower components 102, 104. As discussed above, the central component 182 slidingly engages with the recesses of the upper and lower components 102, 104. In some instances, the central component 182 is fixed to the upper and/or lower components 102, 104 by a locking feature (e.g., set screw) that prevents unwanted movement of the central component relative to the upper and/or lower components 102, 104. In the illustrated embodiment the central component 182 is a compliant core.

As shown, the prosthetic devices and associated methods of the present disclosure facilitate lateral insertion of intervertebral prosthetic devices from a single side of the patient. More specifically, the devices and methods of the present disclosure require access from a single lateral direction, but still facilitate secure engagement of the prosthetic devices with both lateral sides of the vertebrae. Further, a direct lateral approach for lumbar spine surgery offers many benefits. For example, a direct lateral approach can overcome the risks associated with an anterior approach and the space limitations of a posterior approach.

Figure 8:
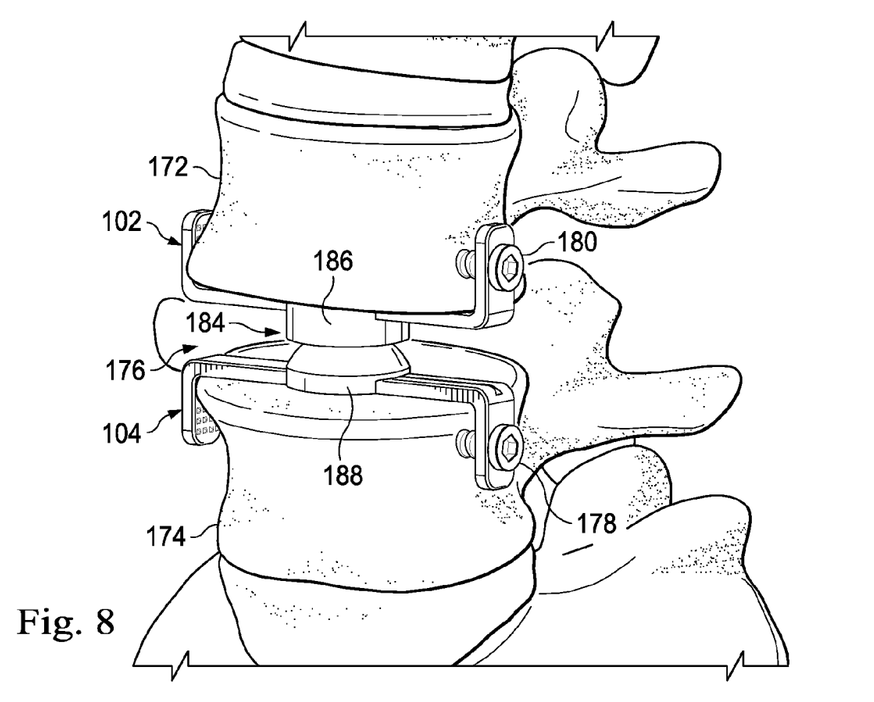
FIG. 8 is a perspective view of a prosthetic device fully implanted between an upper vertebra and a lower vertebra according to another embodiment of the present disclosure.
Figure 9:
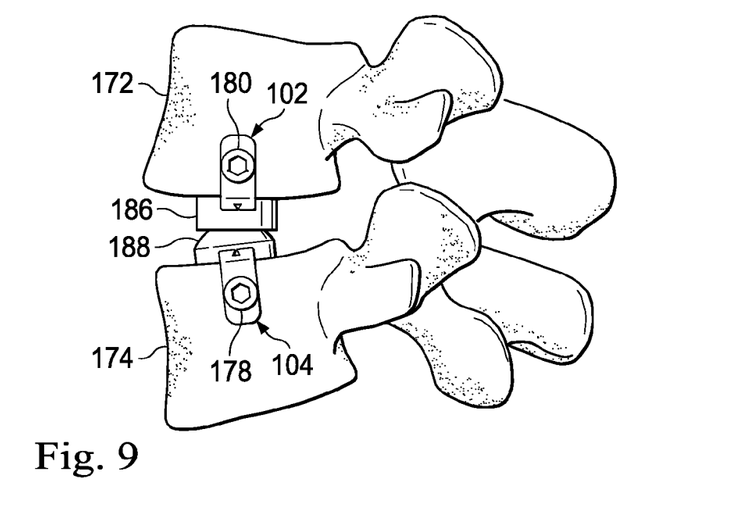
FIG. 9 is a lateral side view of the prosthetic device of FIG. 8 fully implanted between the upper and lower vertebra.

Referring now to FIGS. 8 and 9, shown therein is an alternative embodiment of an intervertebral prosthetic device according to the present disclosure. In that regard, FIG. 8 is a perspective view of the prosthetic device fully implanted between an upper vertebra and a lower vertebra, while FIG. 9 is a lateral side view of the prosthetic device fully implanted between the upper and lower vertebra. As shown, the prosthetic device of FIGS. 8 and 9 includes a central component 184 with a ball-and-socket configuration. The upper portion 186 of the central component 184 defines the socket, while the lower portion 186 defines the ball. In that regard, the upper portion 186 of the central component 184 is engaged with the upper component 102 and the lower portion 188 of the central component 184 is engaged with the lower component 104 such that the central component 184 provides ball-and-socket motion between the upper vertebra 172 and the lower vertebra 174. Generally, the ball-and-socket cores of the present disclosure are made from a variety of materials, including but not limited to stainless steel, titanium carbide, cobalt chrome alloy, ceramic, PEEK, UHMWPE, and other metal, ceramic, polymer, and/or composite materials.

Figure 10:
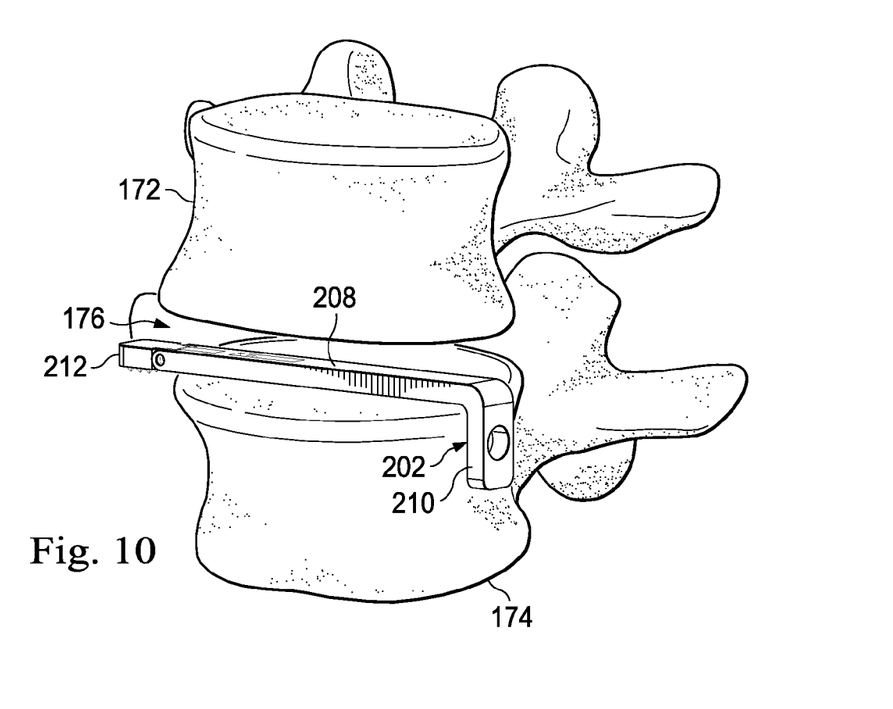
FIG. 10 is a perspective view of an arrangement illustrating implantation of a component of a prosthetic device in an insertion configuration according to one embodiment of the present disclosure.
Figure 11:
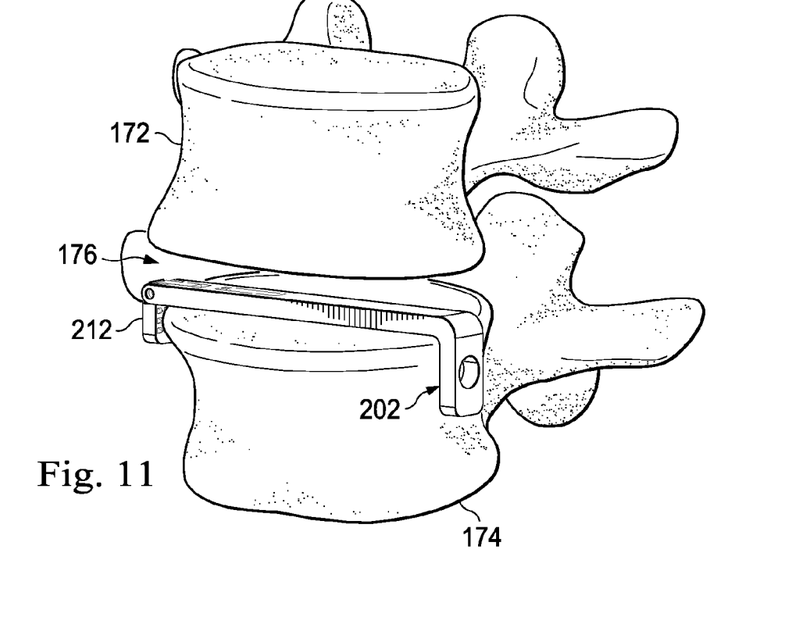
FIG. 11 is a perspective view of the arrangement of FIG. 10 illustrating the component of the prosthetic device fixedly engaged with the lower vertebra in an anchoring configuration.
Figure 12:
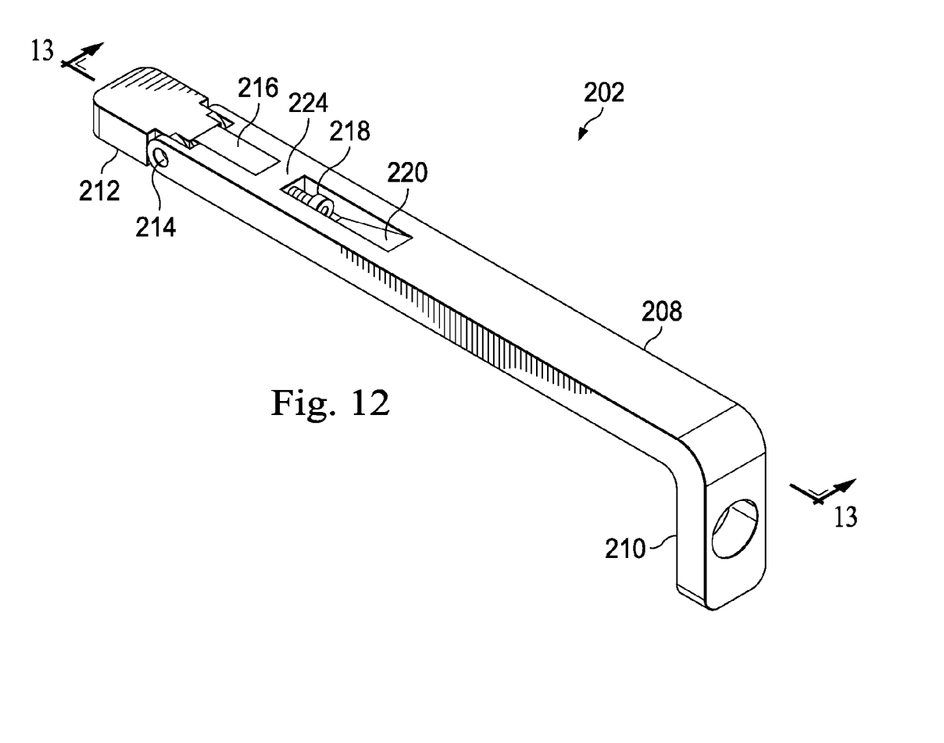
FIG. 12 is a perspective view of the component of the prosthetic device illustrated in FIGS. 10 and 11 in an insertion configuration.
Figure 13:
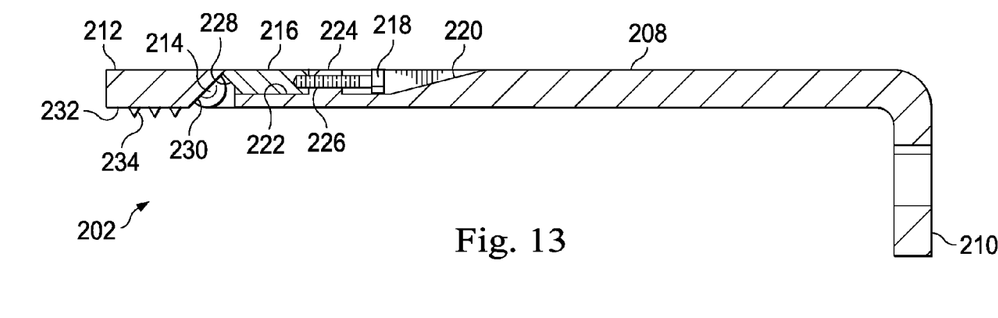
FIG. 13 is a side view of the component of FIG. 12 in the insertion configuration.
Figure 14:
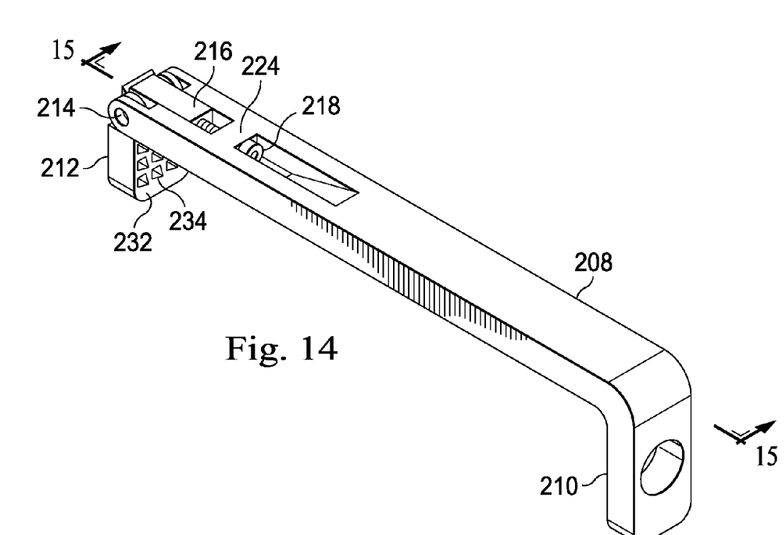
FIG. 14 is a perspective view of the component of FIGS. 12 and 13 in an anchoring configuration.
Figure 15:
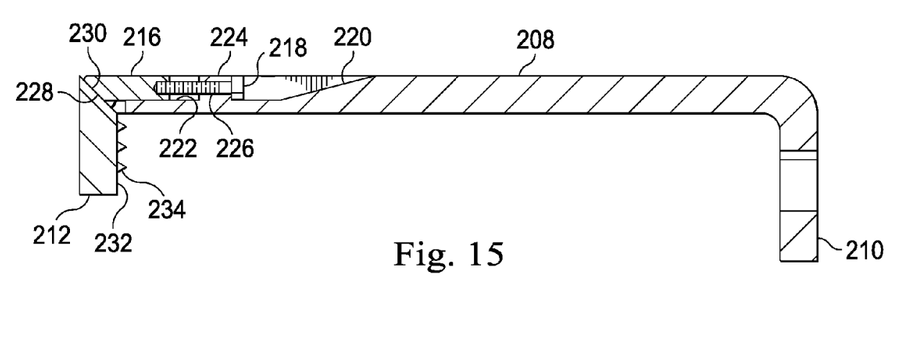
FIG. 15 is a side view of the component of FIGS. 12, 13, and 14 in the anchoring configuration.

Referring now to FIGS. 10, 11, 12, 13, 14, and 15, shown therein is an alternative component 202 that is suitable for use as the upper and lower components of the prosthetic devices of the present disclosure. Specifically, FIG. 10 illustrates the component 202 positioned between a pair of vertebra in an insertion configuration; FIG. 11 illustrates the component 202 fixedly engaged with the lower vertebra in an anchoring configuration; FIG. 12 is a perspective view of the component 202 in the insertion configuration; FIG. 13 is a side view of the component 202 in the insertion configuration; FIG. 14 is a perspective view of the component 202 in an anchoring configuration; and FIG. 15 is a side view of the component 202 in the anchoring configuration.

Referring more specifically to FIG. 10, the component 202 is illustrated in an insertion configuration. In that regard, the component 202 includes a central portion 208, a fixed arm 210, and a pivoting arm 212. As shown, in the insertion configuration the fixed arm extends substantially perpendicular to a longitudinal axis of the central portion 208 while the pivoting arm 212 extends substantially parallel to a longitudinal axis of the central portion. In that regard, the orientation of the pivoting arm 212 in the insertion configuration reduces the height or thickness of the portion of the component 202 that is passed through the intervertebral disc space 176. More specifically, the height or thickness is reduced such that the pivoting arm 212 can be inserted and passed through the disc space 276 without causing damage to the endplates of the vertebrae. In that regard, the component 202 allows similar functionality to the components 102, 104 discussed above but does not require rotation of the entire component.

Referring more specifically to FIG. 11, once the pivoting arm 212 has been inserted and passed across the disc space 276 to a position adjacent the opposing sidewall of the lower vertebra 174, the pivoting arm 212 is pivoted to an anchoring configuration. In the anchoring configuration the pivoting arm 212 extends substantially perpendicular to the central portion 208 and substantially parallel to the fixed arm 210 such that the component 202 is u-shaped. The u-shape of the component 202 when in the anchoring configuration facilitates engagement of the component 202 with both lateral sides of the lower vertebra 174 as shown in FIG. 11.

Referring more specifically to FIGS. 12 and 13, the component 202 is again shown in the insertion configuration. As shown, the component 202 includes a pivot point 214 about which the pivoting arm 212 pivots or rotates. In some embodiments, the pivot point 214 is a pivot pin. The illustrated embodiment utilizes a sliding block 216 and screw 218 to cause rotation of the pivoting arm 212 about the pivot point 214 between the insertion configuration (illustrated in FIGS. 10, 12, and 13) and the anchoring configuration (illustrated in FIGS. 11, 14, and 15). In that regard, the component 202 includes recesses 220 and 222 that contain the block 216 and the screw 218. In that regard, the recesses 220 and 222 are separated by a portion 224 that includes an opening 226. In some instances, the opening 226 is threaded and the screw 218 is cross-pinned to the sliding block 216 so that the sliding block 216 moves with the screw 218. In other instances, the opening 226 is smooth or non-threaded with sufficient clearance for the screw 218 to pass through. In such instances, the screw 218 is cross-pinned to the central portion 208 so that the screw 218 can rotate, but not translate relative to the central portion 208 resulting in movement of the sliding block 216 via a threaded coupling. The screw 218 passes through the opening 226 between the recess 220 (where a head of the screw is positioned) and the recess 222 (where the screw threadingly engages the block 216). As will be discussed in greater detail below, a tapered surface 228 of the block 216 is configured to engage with a surface 230 of the pivoting arm 212 to cause rotation of the pivoting arm between the insertion configuration and the anchoring configuration.

Referring more specifically to FIGS. 14 and 15, the component 202 is shown in the anchoring configuration. Transition of the component 202 and, more particularly, the pivoting arm 212 between the insertion and anchoring configurations is accomplished by rotating the screw 218. In that regard, the threaded engagement of the screw 218 with the sliding block 216 allows the sliding block to be translated along the length of the component 202 through rotation of the screw. In that regard, translation of the sliding block 216 towards the pivoting arm 212 results in the surface 228 of the sliding block engaging with the surface 230 of the pivoting arm. The surfaces 228, 230 are tapered such that as the block 216 is translated towards the pivoting arm 212 engagement of the surfaces 228, 230 causes the pivoting arm to rotate about the pivot point 214 towards the anchoring configuration. As shown, when in the anchoring configuration the surfaces 228, 230 are mated with one another such that they extend substantially parallel to one another. The pivoting arm 212 includes a bone-engaging surface 232 that includes a plurality of engagement features 234. Accordingly, when the pivoting arm 212 is rotated into the anchoring configuration during use the bone-engaging surface 232 and its engagement features 234 will engage the opposing lateral sidewall of the vertebra.

While the pivot arm 212 is generally moved from the insertion configuration to the anchoring configuration, it can likewise be moved from the anchoring configuration to the insertion configuration (e.g., during a revision surgery) by rotating the screw 218 in the opposite direction, which in turn retracts the sliding block 216 allowing the pivot arm 212 to return to the insertion configuration.

In some instances, the component 202 includes a bias mechanism (e.g., a spring) that encourages or biases the pivot arm 212 towards either the insertion or anchoring configuration. In one embodiment, the pivot arm 212 is biased to the anchoring configuration and the component 202 includes a locking feature that holds the pivot arm in the insertion configuration. During use the locking feature is released when transition to the anchoring configuration is desired at which point the bias mechanism urges the pivot arm 212 to the anchoring configuration. In some embodiments, the locking feature can similarly be utilized to secure the pivot arm 212 in the anchoring configuration after transition from the insertion configuration. In some instances, the bias mechanism is utilized in place of the block 216 and screw 218 of the illustrated embodiment. As a general matter, a suitable pivoting or rotation actuating mechanism may be utilized to move the arm 212 between the insertion and anchoring configurations.

Figure 16:
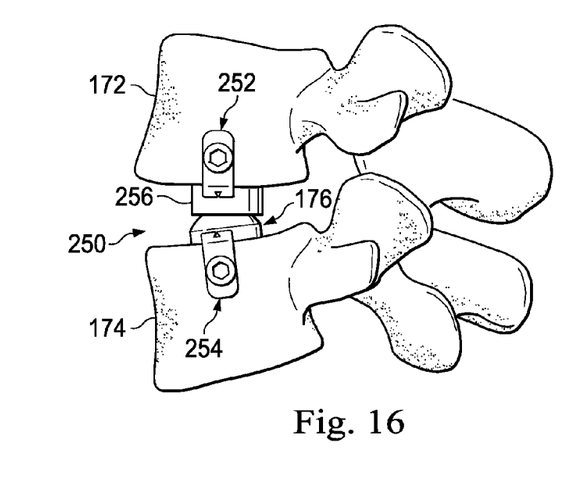
FIG. 16 is a lateral side view of a prosthetic device fully implanted between an upper vertebra and a lower vertebra according to another embodiment of the present disclosure.

Referring now to FIG. 16, shown therein is a prosthetic device 250 fully implanted between an upper vertebra 172 and a lower vertebra 174 according to another embodiment of the present disclosure. The prosthetic device 250 may be substantially similar to any of the prosthetic devices described in the present disclosure by having an upper component 252, a lower component 254, and central component 256, but the engagement of the central component 256 with the upper and lower components 252, 254 facilitates an offset arrangement of the central component relative to one or both of the upper and lower components. In that regard, while a ball-and-socket central component 256 is illustrated any other type of central component (e.g., compliant core, fusion, etc.) may have a similar offset arrangement. Similarly, the upper and lower components 252, 254 may any of the disclosed types, including fixed, pivoting, and/or translating components.

The central component 256 may be offset anteriorly or posteriorly relative to one or both of the upper and lower components 252, 254. Accordingly, where the upper and/or lower components 252, 254 are positioned more anterior or posterior relative to a central axis of the disc space 176 between the upper and lower vertebrae 172, 174, the offset of the central component 256 allows the center of rotation, pivot point, central movement point, or central axis of the prosthetic device to be substantially aligned with the central axis of the disc space. Alternatively, where it is desired to have the center of rotation, pivot point, central movement point, or central axis of the prosthetic device 250 to be offset anteriorly or posteriorly relative to the central axis of the disc space, the upper and lower components 252, 254 can be engaged with the upper and lower vertebrae 172, 174 in substantial alignment with the central axis of the disc space 176 and the offset of the central component 256 relative to the upper and lower components 252, 254 provides the desired positioning of the center of rotation, pivot point, central movement point, or central axis of the prosthetic device 250. In the illustrated embodiment of FIG. 16, the prosthetic device 250 is shown with the central component 256 positioned posteriorly relative to the upper and lower components 252, 254.

Referring now to FIGS. 17 and 18, shown therein is an endplate component 260 of prosthetic device according to another embodiment of the present disclosure. In that regard, FIG. 17 is a perspective view of the endplate component 260 in a lengthened configuration, while FIG. 18 is a perspective view of the endplate component 260 in a shortened configuration. As shown, the endplate component 260 is adjustable between the lengthened and shortened configurations such that the distance between the arms is modifiable to fit a variety of vertebra sizes and/or provide a secure fit to a particular vertebra. In that regard, the endplate component 260 utilizes a sliding block configuration similar to those discussed above in the context of the pivoting arm of component 202. The endplate component includes a proximal arm 262 and a distal arm 264, where the distal arm 264 is movable relative to the proximal arm 262 via the sliding block configuration. In that regard, the sliding block configuration includes a block 266 that is fixedly attached to the distal arm 264 such that the distal arm moves with the block 266. The block 266 and the distal arm 264 are an integral or monolithic piece in some instances. The block 266 mates with a screw 268. Rotation of the screw 268 causes the block 266 and, thereby, the arm 264 to translate along the length of the endplate component 260.

Accordingly, in use the endplate component 260 can be inserted into the disc space between a pair of vertebrae in the elongated configuration (FIG. 17). Once properly positioned relative to the vertebra the endplate component 260 is to engage the screw 268 can be rotated to cause the block 266 to translate proximally, reducing the distance between the arms 262, 264. The screw 268 is rotated until secure engagement with the sidewalls of the vertebra is obtained, which is generally illustrated by the shortened configuration (FIG. 18). It is understood that the amount of shortening of the endplate component 260 needed to provide a secure engagement depends on the size of the vertebra to which the component is to be secured.

The present disclosure provides top and bottom endplates that engage the lateral walls of the vertebral bodies for stability and incorporate a compliant core, ball and socket core, fusion-cage core, or any other suitable type of motion-preserving or fusion cores. The endplate designs allow insertion through a unilateral approach yet still have engagement on both sides of the vertebral body to provide stability and reduce the risk of subsidence. In some instances, saddle style endplates are inserted and then rotated 90 degrees to engage the lateral walls of the vertebral bodies. In other instances, hinged style endplates are inserted in a first orientation and then at least one end portion is pivoted to a second orientation so that the endplates engage the lateral walls of the vertebral bodies.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the embodiment. Accordingly, it is appropriate that the appended claims be construed broadly and in a manner consistent with the scope of the present disclosure.

What is claimed is:

1. An intervertebral prosthetic device comprising: an upper component for engaging an upper vertebra, the upper component having an elongated central portion extending along a first longitudinal axis, the elongated central portion bounded on a first end by a first arm extending substantially perpendicular to the first longitudinal axis and bounded on an opposing second end by a second arm extending substantially perpendicular to the first longitudinal axis, wherein the first arm is configured to engage a first lateral sidewall of the upper vertebra, the first arm including an outer surface opposite a bone engaging surface, the outer surface and the bone engaging surface having an opening extending therethrough, the opening configured to receive a fastener for securing the first arm to the first sidewall of the upper vertebra, the second arm is configured to engage a second lateral sidewall of the upper vertebra, the second arm having an outer surface opposite a bone engaging surface, the second arm outer surface having no opening and the second arm bone engaging surface including a surface treatment having a plurality of bone-engaging projections for encouraging engagement of the second arm with the second sidewall of the upper vertebra, and the elongated central portion is sized to extend across an endplate of the upper vertebra between the first lateral sidewall and the second lateral sidewall of the upper vertebra, and further wherein a width of the upper component is substantially constant such that the central portion, the first arm, and the second arm each have a width substantially equal;

an lower component for engaging an lower vertebra, the lower component having an elongated central portion extending along a second longitudinal axis, the elongated central portion bounded on a first end by a first arm extending substantially perpendicular to the second longitudinal axis and bounded on an opposing second end by a second arm extending substantially perpendicular to the second longitudinal axis, wherein the first arm is configured to engage a first lateral sidewall of the lower vertebra, the first arm having an outer surface opposite a bone engaging surface, the outer surface and the bone engaging surface having an opening configured to receive a fastener for securing the first arm to the first sidewall of the lower vertebra, the second arm is configured to engage a second lateral sidewall of the lower vertebra, the second arm having an outer surface opposite a bone engaging surface, the second arm outer surface having no opening and the second arm bone engaging surface including a surface treatment having a plurality of bone-engaging projections for encouraging engagement of the second arm with the second sidewall of the lower vertebra, and the elongated central portion is sized to extend across an endplate of the lower vertebra between the first lateral sidewall and the second lateral sidewall of the lower vertebra, and further wherein a width of the lower component is substantially constant such that the central portion, the first arm, and the second arm each have a width substantially equal; and a central component for positioning between the upper component and the lower component within an intervertebral space between the upper and lower vertebrae.

2. The intervertebral prosthetic device of claim 1, wherein the elongated central portion, first arm, and second arm of the upper component are integrally formed.

3. The intervertebral prosthetic device of claim 1, wherein the central component engages each of the upper and lower components with a dovetail interface.

4. The intervertebral prosthetic device of claim 3, wherein the central component is a motion-preserving device.

5. The intervertebral prosthetic device of claim 3, wherein the central component is a fusion device.

6. The intervertebral prosthetic device of claim 1, wherein the fastener for securing the first arm to the first sidewall of the upper vertebra is a bone screw.

7. The intervertebral prosthetic device of claim 1, wherein the second arm of the upper component is movable between an insertion position where the second arm extends substantially parallel to the first longitudinal axis and an anchoring position where the second arm extends substantially perpendicular to the first longitudinal axis.

8. The intervertebral prosthetic device of claim 7, wherein the upper component includes an actuator adjacent to the second end of the upper component, the actuator configured to pivot the second arm between the insertion position and the anchoring position.

9. The intervertebral prosthetic device of claim 1, wherein the central portion of the upper component is configured to be adjustable to modify a distance between the first arm and the second arm.

10. The intervertebral prosthetic device of claim 9, wherein the first arm of the upper component is fixed to extend substantially perpendicular to the longitudinal axis.

11. A prosthetic system comprising:
a first component for engaging a first vertebra, the first component having an elongated central portion extending along a first longitudinal axis, the elongated central portion bounded on a first end by a first arm extending substantially perpendicular to the first longitudinal axis and bounded on an opposing second end by a second arm, the second arm movable between an insertion position wherein the second arm extends substantially parallel to the first longitudinal axis and an anchoring position wherein the second arm extends substantially perpendicular to the first longitudinal axis, wherein the first arm is configured to engage a first lateral sidewall of the first vertebra, the second arm is configured to engage a second lateral sidewall of the first vertebra when in the anchoring position, and the elongated central portion is sized to extend across an endplate of the first vertebra between the first lateral sidewall and the second lateral sidewall of the first vertebra, and further wherein the first component includes an actuator positioned adjacent to the second end, the actuator configured to pivot the second arm between the insertion position and the anchoring position, the actuator including a sliding block and a screw configured such that rotation of the screw causes movement of the sliding block along the first axis;

a second component for engaging a second vertebra, the second component having an elongated central portion extending along a second longitudinal axis, the elongated central portion bounded on a first end by a first arm extending substantially perpendicular to the first longitudinal axis and bounded on an opposing second end by a second arm, wherein the first arm is configured to engage a first lateral sidewall of the second vertebra, the second arm is configured to engage a second lateral sidewall of the second vertebra, and the elongated central portion is sized to extend across an endplate of the second vertebra between the first lateral sidewall and the second lateral sidewall of the second vertebra; and a central component for positioning between the first component and the second component within an intervertebral space between the first and second vertebrae.

12. The prosthetic system of claim 11, wherein the second arm of the second component is movable between an insertion position where the second arm extends substantially parallel to the second longitudinal axis and an anchoring position where the second arm extends substantially perpendicular to the second longitudinal axis.

13. The prosthetic system of claim 11, wherein at least the screw of the actuator is positioned within a recess in the elongated central portion.

14. The prosthetic system of claim 11, wherein the central component engages at least the first component with a dovetail interface.

15. An intervertebral device comprising:
a component for engaging a first vertebra, the component having an elongated central portion extending along a first longitudinal axis, the elongated central portion bounded on a first end by a first arm extending substantially perpendicular to the first longitudinal axis and bounded on an opposing second end by a second arm, the second arm movable between an insertion position wherein the second arm extends substantially parallel to the first longitudinal axis and an anchoring position wherein the second arm extends substantially perpendicular to the first longitudinal axis, wherein the first arm is configured to engage a first lateral sidewall of the first vertebra, the second arm is configured to engage a second lateral sidewall of the first vertebra when in the anchoring position, and the elongated central portion is sized to extend across an endplate of the first vertebra between the first lateral sidewall and the second lateral sidewall of the first vertebra,
wherein the component includes a sliding block adjacent to the second end, the sliding block movable and having a tapered surface configured to engage with a surface of the movable second arm to cause rotation of the movable second arm between the insertion position and the anchoring position, and wherein the device is U-shaped in the anchoring position.

16. The intervertebral device of claim 15, wherein the sliding block secures the second arm in the anchoring position.

17. The intervertebral device of claim 16, wherein the component includes a threaded member in communication with the sliding block, wherein rotation of the threaded member causes movement of the sliding block to pivot the second arm between the insertion position and the anchoring position.

18. The intervertebral device of claim 17, wherein the sliding block and the threaded member are positioned within one or more recesses in the elongated central portion.

19. The intervertebral device of claim 18, wherein the first arm of the component includes an opening for receiving a fastener for securing the first arm to the first lateral sidewall of the first vertebra.

20. The intervertebral device of claim 19, wherein the second arm of the component includes a surface treatment including a plurality of bone engaging projections for encouraging engagement of the second arm with the second lateral sidewall of the second vertebra.

* * * * *